(12) United States Patent
Forsell (10) Patent No.: US 8,644,940 B2
(45) Date of Patent: Feb. 4, 2014

(54) BRAIN STIMULATION

(75) Inventor: Peter Forsell, Zug (CH)

(73) Assignee: Milux Holding SA, Luxembourg (LU)

( * ) Notice: Subject to any disclaimer, the term of this patent is extended or adjusted under 35 U.S.C. 154(b) by 262 days.

(21) Appl. No.: 12/990,310

(22) PCT Filed: Apr. 30, 2009

(86) PCT No.: PCT/EP2009/003150
§ 371 (c)(1),
(2), (4) Date: Oct. 29, 2010

(87) PCT Pub. No.: WO2009/132855
PCT Pub. Date: Nov. 5, 2009

(65) Prior Publication Data
US 2011/0046694 A1    Feb. 24, 2011

Related U.S. Application Data

(60) Provisional application No. 61/071,471, filed on Apr. 30, 2008.

(51) Int. Cl.
*A61N 1/00* (2006.01)
*A61B 5/04* (2006.01)

(52) U.S. Cl.
USPC ............................ 607/45; 607/118; 600/378

(58) Field of Classification Search
USPC .................................. 600/378; 607/45, 118
See application file for complete search history.

(56) References Cited

U.S. PATENT DOCUMENTS

| | | | |
|---|---|---|---|
| 5,304,206 A | 4/1994 | Baker et al. | |
| 2004/0102828 A1 | 5/2004 | Lowry et al. | |
| 2004/0143300 A1 | 7/2004 | Rogers | |
| 2005/0107716 A1 | 5/2005 | Eaton et al. | |
| 2005/0277824 A1 | 12/2005 | Aubry et al. | |
| 2006/0058627 A1 | 3/2006 | Flaherty et al. | |
| 2006/0173510 A1 | 8/2006 | Besio et al. | |
| 2007/0135877 A1 | 6/2007 | Pringle | |
| 2007/0179570 A1 | 8/2007 | De Taboada et al. | |
| 2007/0299370 A1* | 12/2007 | Bystritsky | 601/2 |

FOREIGN PATENT DOCUMENTS

| WO | WO 98/07373 | 2/1998 |
|---|---|---|
| WO | WO 99/62599 | 12/1999 |
| WO | WO 2005/058157 | 6/2005 |
| WO | WO 2006/053114 | 5/2006 |
| WO | WO 2008/005478 | 1/2008 |

OTHER PUBLICATIONS

International Search Report for PCT/EP2009/003150, mailed Feb. 8, 2010.
Written Opinion of the International Searching Authority for PCT/EP2009/003150, mailed Feb. 8, 2010.

* cited by examiner

*Primary Examiner* — Nicole F Lavert
(74) *Attorney, Agent, or Firm* — Nixon & Vanderhye PC (57) ABSTRACT

A therapeutic brain stimulation system comprises at least two stimulation signal emitters generating stimulation signals from different positions towards a common target region in a patient's brain. While the signal intensity of each stimulation signal is much too low to cause stimulation, the accumulated stimulation signals cause a stimulation and, thus, a therapeutic effect in the neuronal brain cells of the target region. The stimulation signals accumulating in the target region are adjustable so as not to negatively affect the anatomic structure of neuronal brain cells in the target region.

31 Claims, 7 Drawing Sheets

BRAIN STIMULATION

This application is the U.S. national phase of International Application No. PCT/EP2009/003150 filed 30 Apr. 2009, which designated the U.S. and claims the benefit of U.S. Provisional Appln. No. 61/071,471 filed 30 Apr. 2008, the entire contents of each of which are hereby incorporated by reference.

BACKGROUND OF THE INVENTION

The present invention relates to the stimulation of regions of a patient's brain for therapeutic purposes and, in particular, to a therapeutic brain stimulation system, a method of mounting such system relative to or on the patient's cranium, a method of adjusting the system once it has been mounted on the patients head and a therapeutic method of stimulating the brain using such system.

It is known to stimulate the human brain electrically by advancing electrodes into a specific brain region to be stimulated. In micro stimulation therapy, extremely fine glass pipettes are used. These methods are highly invasive.

It is also known to stimulate the brain with light irradiation. In this method, specific DNA fragments are introduced in the cell walls of neurons within the brain. The DNA fragments are adapted to produce light-sensitive proteins. Those neurons expressing such protein are stimulated by illumination. Illumination is carried out through a glass plate covering a surgically created hole in the patent's cranium. Thus, in this method the cranium is permanently open to allow light to be transmitted. Only outer brain areas can be stimulated by the illumination.

Furthermore, a non-invasive therapeutic brain stimulation method is known which is called "transcranial magnetic stimulation" (TMS). In this method, a circular or figure-eight type coil is used to create an electromagnetic field inside the brain, thereby inducing a current in the brain's neurons, in particular in those neurons having the axons parallel to the electric field. The position and orientation of the coil as well as the duration and intensity of stimulation can be varied. In so-called repetitive TMS (rTMS) a sequence of stimulus pulses is provided, the pulse length, the time between the pulses, the duration of the stimulation sequence and the number of stimulation sequences being varied to achieve different therapeutic results. A plurality of coils can be used to stimulate different brain regions to achieve a combinatory therapeutic effect. However, as the distance to the coil increases linearly, the intensity of the electromagnetic field decreases exponentially. Also, the heat dissipation close to the patient's head can cause problems. The application of TMS and rTMS is thus limited to the outer areas of the brain, i.e. to the cerebral cortex, in proximity to the parietal and occipital cranial bone structure.

It is further known, but not in the context of brain stimulation, to subject the human brain to ultrasonic waves. The ultrasonic waves are applied to destroy brain tumours by non-invasive surgery. A complex network of a great number of small ultrasound emitters, such as more than 300 senders, are applied to the patient's head from the outside thereof and directed towards a very limited target area of e.g. 1 mm in size within the patient's brain. The little size and equal distribution prevents regions of the brain outside the target area from heating up above a critical cell temperature. However, where the destroyed tumour cells cannot be removed by internal body functions, the cranium has nevertheless to be opened for removing the dead tumour cells, unlike related methods of destroying kidney stones where the fragments of the ultrasonically destroyed stones are discarded naturally.

Alternatively, the target can be irradiated stereo-tactically (DE 196 14 643 A1). In this method, the patient and/or an irradiation source are rotated relative to a target centre within the patient's brain. This way, the target is hit from different sides over time, the radiation ultimately leading to the destruction of the tumour cells.

SUMMARY OF THE INVENTION

It is an object of the present invention to propose a new system and method to stimulate limited regions inside a patient's brain for therapeutic purposes without the need to penetrate into the patient's brain, i.e. preferably completely non-invasively. This system and method permit brain activity to be stimulated in one or more limited brain regions of e.g. depressive or epileptic patients.

A therapeutic brain stimulation system according to the present invention comprises at least two and preferably three or more stimulation signal emitters. The number of stimulation signal emitters may even be 100 or more. The stimulation signal emitters are directed from different positions outside the patient's brain onto a common target region within the patient's brain so as to provide an accumulated stimulating effect on that target region. The intensity of the stimulation signal of each of the emitters is adjusted so low that it does not cause stimulation of a brain region other than the target region where the stimulating effects of all signal emitters are accumulated. In addition, the signal emitters are adjustable such that the accumulated stimulating signals in the target region do not negatively affect the anatomic structure of neuronal brain cells. For therapeutic purposes it would be undesirable to destroy the brain cells to be stimulated. In order to achieve these goats, it can be necessary to employ a great number of signal emitters with a sufficiently low stimulation signal intensity. The required number of signal emitters largely depends upon the type of signal emitters used.

Such arrangement allows non-invasive stimulation of specific target regions deep inside the patient's brain. However, this does not exclude permanently implanting a catalyst element, such as a metal piece, in the patient's brain to increase the effectiveness of the accumulated stimulation signals.

Generally speaking, a current may be induced in or near neuronal brain cells in the patient's brain in order to stimulate the brain. The induced electrical current may cause a chemical reaction to occur in the neuronal brain cells, thereby achieving the therapeutic effect. With other stimulation signals, such chemical reaction in the neuronal brain cells can be provoked either directly or in a different manner indirectly. The stimulation signals may likewise comprise electromagnetic radiation, sound waves, current inducing electromagnetic fields and others.

Where electromagnetic radiation is employed, this may include light waves with a wavelength in the range between infrared and ultraviolet or waves with a wavelength longer than infrared light. It is also possible to use electromagnetic radiation comprising microwaves. Preferably, the electromagnetic radiation signals are emitted in the form of beams which are directed to cross each other in the target region. Focusing devices may help to concentrate the beam onto the target region.

Where sound waves are used as the stimulation signal, these are preferably ultrasonic sound waves. In this case it is advantageous when sound wave signal emitters are arranged at an equal distance from the target region or at least at a phase-correct distance relative to the target region.

Where the signal emitters are adapted to emit the individual stimulation signals in the form of electromagnetic fields, it is advantageous when the electromagnet fields overlap each other in a manner such that the current directions of the currents induced in the target region are co-linear.

Just as a basic example, the signal emitter may comprise a helical winding with a current flowing through the helical winding. The helical winding winds around a symmetry axis, which axis is then directed through the brain target region to be stimulated. A more detailed explanation of how a signal emitter is accurately positioned relative to the target region will follow below.

There are various alternatives for mounting the emitters on the patient's head. For instance, the signal emitters may be permanently mounted to the patient's cranium either directly or indirectly. For instance, the signal emitters may be fixed directly in the cranial bone structure. Their position relative to each other and relative to the patient's brain is thereby permanently defined. In this respect, it may be sufficient that the signal emitters, i.e. their fixation parts, penetrate only the hard outer layer of the cranial bone structure. It can be advantageous, however, when the signal emitters penetrate the cranial bone structure completely. This is particularly advantageous when the signal emitters are of a type where the cranial bone would severely hinder the stimulation signals from penetrating into the patient's brain.

The signal emitters may comprise one or more screw threads for fixation in the cranial bone structure. Such screw threads may be provided on an outer surface of the signal, emitters, more specifically, the signal emitters may be contained in a mounting tube with the screw threads provided on an outer surface of the mounting tube. The orientation of the signal emitter inside the mounting tube is adjustable, as will be explained in more detail below.

It is further advantageous when the signal emitters being fixed in the cranial bone structure are implanted subcutaneously, i.e. so as not to penetrate the skin after implantation. This will allow the patient to live a relatively normal life. That is, once the signal emitters have been accurately adjusted to the target region in the patient's brain so as to allow for stimulation of a particular brain region whenever need arises, such as in the case of epileptic patients, the patient can continue to live with the signal emitters fixedly mounted subcutaneously in the cranial bone structure.

Where direct fixation of the signal emitters in the cranial bone structure is not desired, they can be positioned at least adjacent the patient's cranial bone and held in contact with the cranial bone by connecting them to a common support structure which provides sufficient elasticity and stiffness. More specifically, when the signal emitters mounted on the common support structure are arranged at positions on opposite sides of the patient's head, they will be held in contact with the patient's cranial, bone due to the elasticity and stiffness of the support structure. Of course, the likelihood of a signal emitter being unintentionally displaced is somewhat increased in this embodiment.

Alternatively, the common support structure rather than the signal emitters is mounted on the patient's cranium. In this case, the signal emitters are arrangeable on the support structure so that their individual stimulating signals can be emitted from different positions of the support structure towards the common target region in the patient's brain so as to provide said accumulated stimulating effect on the target region. Again, the mounting of the support structure on the patient's cranium can be permanent and, thus, relatively secure against unintentional displacement, or non-permanent, i.e. detachable. In the latter case of detachably mounting the support structure on the patient's cranium, a padding may be provided between the support structure and the patient's skin. More specifically, the support structure may be integrated into a helmet-like hat.

In the other case of permanently mounting the support structure on the patient's cranium, support legs of the support structure may be fixedly mounted in the cranial bone structure in the same manner as described above in relation to the signal emitters fixed in the cranial bone structure, or the support legs may be positioned adjacent the patient's cranial bone at positions on opposite sides of the patient's head and held in contact with the patient's cranial bone due to the elasticity and stiffness provided by the support structure.

An adjustment device may be provided for adjusting the relative positions of the signal emitters on the support structure such that their individual stimulation signals accumulate in the target region. More specifically, the signal emitters may be mounted on the support structure so as to be pivotal about one or preferably at least two pivoting axes. Furthermore, the support structure may comprise curved beams along which the signal emitters are displaceable, such beams preferably embracing an angle of curvature of at least about 180°.

In addition, the signal emitters may be mounted on the support structure so as to be movable towards and away from the target region, i.e. perpendicular to the patient's cranium. This is particularly relevant where the intensity of the stimulation signals emitted by the signal emitters decreases exponentially with the travel distance to the target region. Moving the signal emitters away from the patient's cranium will cause the stimulation signal to enter the patient's cranium with a signal intensity which is sufficiently low not to cause any damage in the neuronal brain cells and which does not decrease very much over the travel distance within the patient's brain.

As mentioned above, an adjustment device may be provided to adjust the position of the signal emitters relative to the target region in the patient's brain and/or to adjust the relative positions of the signal emitters on the common support structure. A preferred embodiment of such adjustment device wilt be described in the following. The adjustment device may include at least one position adjusting motor mechanically connected to the signal emitter. The signal emitter may comprise, just as an example, a primary coil for transferring wireless stimulation signals. An external control unit may control the adjustment device to adjust the position of the signal emitter/primary coil relative to the target region. The position controller may be coordinated with a 3-D brain imaging system by means of an appropriately programmed processing system. The position adjusting motor may include a position sensor for providing position information to the external control unit. A housing may enclose the position adjusting motor and the primary coil to allow free movement of the primary coil.

The position adjusting motor may further include at least one distance adjusting motor for adjusting the distance between the signal emitter/primary coil and the target region. The distance adjusting motor may include a distance adjusting linear motor for displacing the primary coil in a first direction substantially perpendicular to the patient's cranium. The distance adjusting motor may then include a first distance adjusting rotation motor for displacing the primary coil in a second direction substantially parallel to the patient's cranium, by turning the primary coil around a first distance adjustment axis. The distance adjusting motor may also include a second distance adjusting rotation motor for displacing the primary coil in the second direction, by turning the primary coil around a second distance adjustment axis which is substantially parallel to but separate from the first distance adjustment axis.

Alternatively, the distance adjusting motor may include at least one angle adjusting motor for adjusting the angle between the primary coil and the target region. In this case, the primary coil may e.g. comprise a helical winding around a symmetry axis, and the angle adjusting motor adjusts the angle by turning the symmetry axis of the primary coil relative to a corresponding symmetry axis of the target region. The angle adjusting motor may also include a first angle adjusting motor for turning the primary coil around a first angle adjustment axis. The first angle adjustment axis may be substantially parallel to the patient's cranium, and the first angle adjusting motor will then turn the primary coil in a first plane substantially perpendicular to the patient's cranium. The first angle adjusting motor may be a linear motor or a rotation motor.

The angle adjusting motor may also include a second angle adjusting motor for turning the primary coil around a second angle adjustment axis perpendicular to the first angle adjustment axis. The second angle adjustment axis may be substantially parallel to the patient's cranium, and the second angle adjusting motor will then turn the primary coil in a second plane substantially perpendicular to the patient's cranium and substantially perpendicular to the first plane. The second angle adjusting motor may be a linear motor or a rotation motor.

The position adjustment device may further include a first ring member inside which the signal emitter/primary coil is mounted by means of opposite first rotation bearings coaxial with the second angle adjustment axis, and a second ring member inside which the first ring member is mounted by means of opposite second rotation bearings coaxial with the first angle adjustment axis, such that the primary coil can be tilted in any direction as a gyro.

In addition to the position controller for controlling the adjustment of the positions of the signal emitters relative to the target region to be stimulated, the control unit may further include a signal emission controller for controlling the generation of stimulating signals emitted by the signal emitters. The signal emission controller may be used to control in particular the timing, sequence, intensity, frequency and/or duration of the emitted stimulating signals.

The signal emission controller may be operable by the patient. For instance, the signal emission controller may comprise a hand-held wireless remote control adapted to turn on and off the system or it may comprise a manually operable switch for turning on and off the system, the switch preferably being subcutaneously implanted so as to be manually operable from outside the patient's body. A functional and/or physical parameter sensor for sensing functional parameters of the system and/or physical parameters of the patient may be provided in connection with the signal emission controller, so that the signal emission controller can adjust the stimulating signals in response to the sensor signals.

The signal emission controller may be specifically adapted to vary the intensity of the stimulating signals over time, in particular cyclically. More specifically, the signal emission controller may be adapted to control the emission of the stimulating signals in the form of pulse signals.

It is also possible to control stimulation of different areas of the target region at a time. The different target region areas may be sequentially stimulated, or the stimulation may be shifted over time from one target region area to another target region area.

In a preferred embodiment of the invention, the signal emission controller controls the stimulation to intermittently stimulate the target region or target region areas in the brain with pulses which preferably form pulse trains. At least a first area and a second area of the target region may repeatedly be stimulated with a first pulse train and a second pulse train, respectively, such that over time the first and second pulse trains are shifted relative to each other. For example, the first area may be stimulated with the first pulse train while the second area is not stimulated with said second pulse train, and vice versa. Alternatively, the first and second pulse trains may be shifted relative to each other such that the first and second pulse trains at least partially overlap.

The pulse trains can be configured in many different ways. More specifically, the signal emission controller may control the stimulation by varying the amplitudes of the pulses of the pulse trains, the duty cycle of the individual pulses of each pulse train, the width of each pulse of the pulse trains, the length of each pulse train, the repetition frequency of the pulses of the pulse trains, the repetition frequency of the pulse trains, the number of pulses of each pulse train, and/or the off time periods between the pulse trains. Several pulse trains of different configurations may be employed to achieve the desired effect.

In the case that the signal emission controller controls the stimulation device to vary the off time periods between pulse trains that stimulate a specific area of the target region, it is possible to control each off time period between pulse trains to last long enough so as to restore a good stimulation climate in the neuronal cells of said specific area while the area is not stimulated.

It has been mentioned above that the system may comprise a remote control, in particular operable by the patient, comprising a first part to be mounted on the patient's cranium along with the signal emitters and a second part for remote communication with the first part. Wiring between the first and second parts of the control unit can be dispensed with, if desired. Data may be transferred between the first part of the control unit and the signal emitters either wirelessly or via galvanic coupling. Also, energy may be supplied to the signal emitters or to the first part of the control unit either galvanically or wirelessly. In the latter case, at least one energy transformer may be provided, connected to the signal emitters or the first part of the control unit, for transforming the wireless energy into electric energy and for supplying the electric energy directly or indirectly to the signal emitters, and an energy transmitter may be provided for wirelessly transmitting the energy to the at least one energy transformer. As regards the control unit, the first part of the control unit mounted to the patient's cranium along with the signal emitters may be programmable via the second part of the control unit, and the second part of the control unit may be adapted to transmit feedback signals to the first part of the control unit. The feedback signal may relate e.g. to the aforementioned functional and physical parameters of the system and patient, respectively.

The invention will now be described in more detail in context with some preferred embodiments of the invention as shown in the accompanying drawings.

DETAILED DESCRIPTION OF THE DRAWINGS

Figure 1:
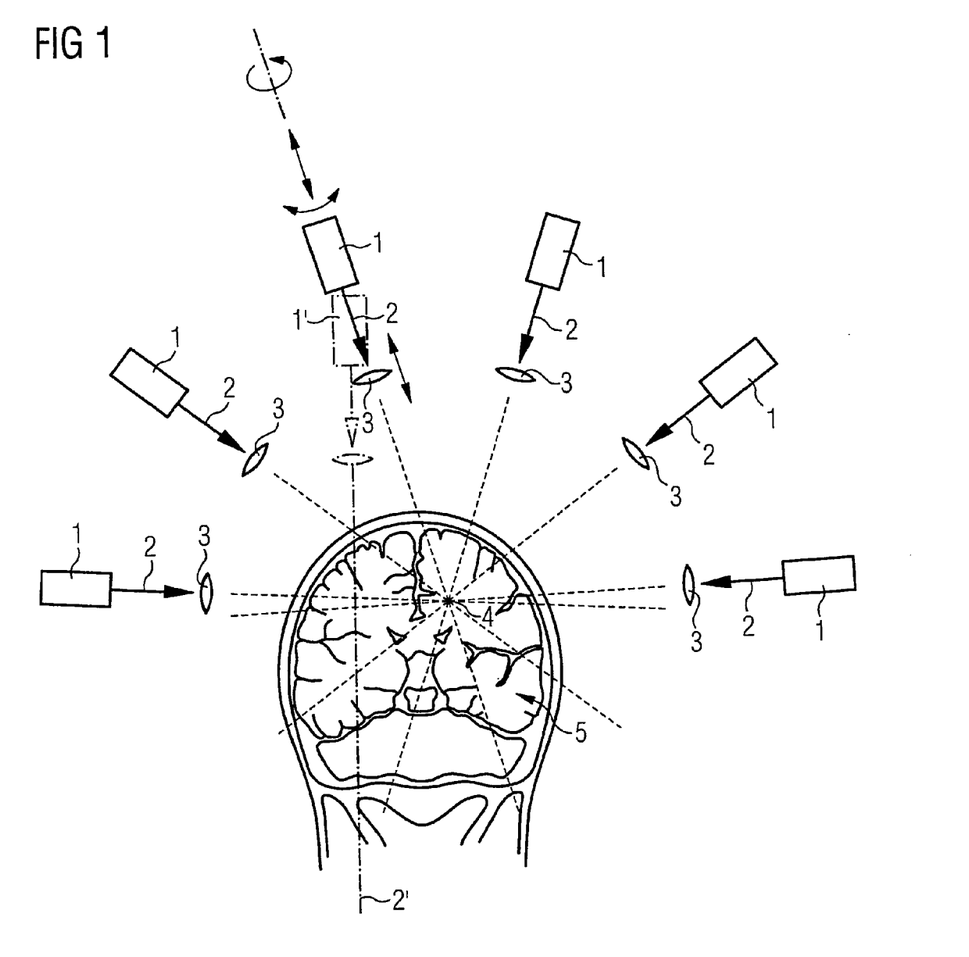
FIG. 1 shows very schematically a first embodiment of a brain stimulation system.

FIG. 1 schematically shows a first embodiment of a brain stimulation system. The brain stimulation system that is shown here includes six signal emitters 1, as an example. The signal emitters 1 are adapted to emit electromagnetic radiation in the form of beams 2. A lens system 3 is schematically shown as a focusing means for each of the signal emitters 1 and is displaceable along the axis of the beam 2 so as to concentrate the radiation on a common target region 4 within the patient's brain 5. Each of the signal emitters 1 is individually adjustable so that it can be directed to any desired location within the patient's brain 5. The pivoting axis, longitudinal displacement axis and rotational axis along which the signal emitters 1 can be displaced are indicated by arrows in respect of only one of the signal emitters 1. Shown by dotted lines and designated with reference numeral 1' is a signal emitter that has been displaced so as to direct the corresponding beam 2' onto a different region in the patient's brain 5.

Figure 2:
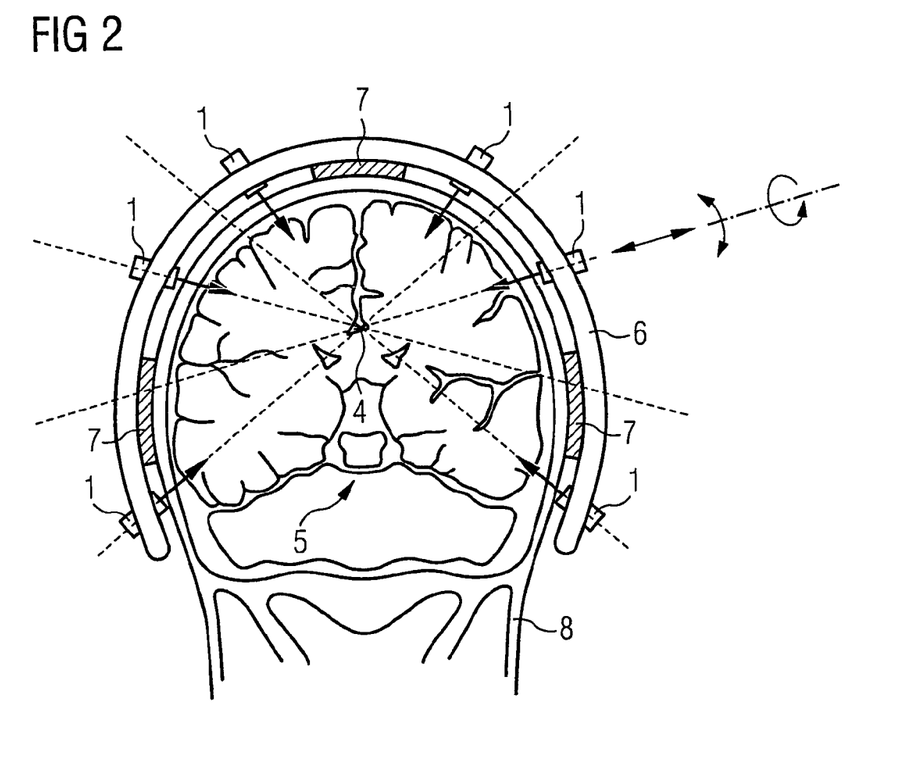
FIG. 2 shows a second embodiment of a brain stimulation system.

FIG. 2 shows a second, more specific embodiment of a brain stimulation system, with the signal emitters 1 being mounted on a common support structure 6. Padding 7 provided at various positions between the support structure 6 and the patient's cranium 8 ensures a snug fit and comfortable seat of the support structure 6 on the patient's head. The padding is chosen sufficiently large to guarantee a stable support without causing pain to the patient's skin. The support structure 6 itself is elastic but sufficiently stiff to urge the paddings 7 against the skin on the patient's cranium 8. The signal emitters 1 are mounted on the support structure 6 so as to be freely movable in any direction. Accordingly, they are mounted pivotally on a pivot axis substantially parallel to the patient's cranium, they are further rotatable about a rotating axis perpendicular to the pivot axis and, possibly, they are also axially displaceable along the rotating axis. This allows all of the signal emitters 1 to be directed onto a common target region 4 within the patient's brain 5.

Figure 3A:
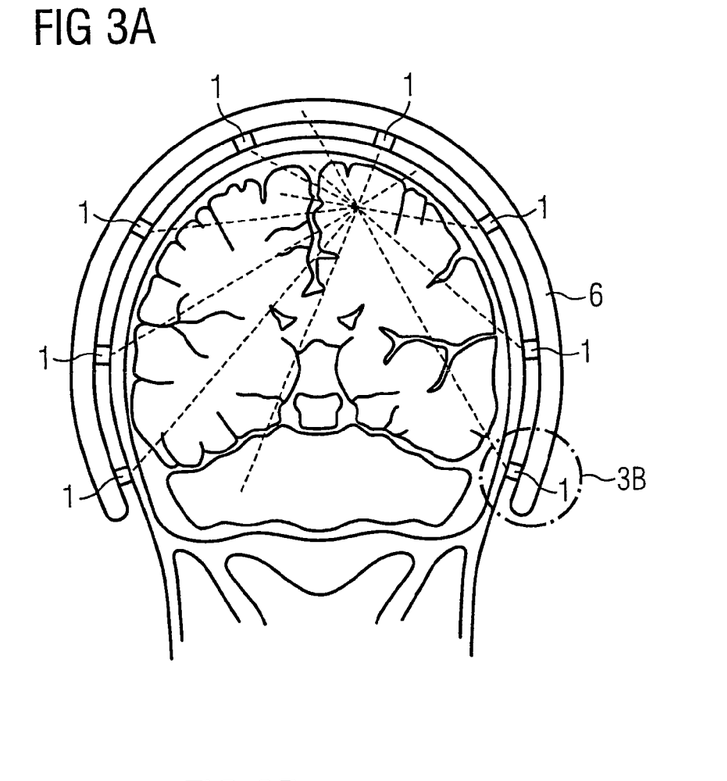
FIGS. 3A and 3B show a third embodiment of a brain stimulation system.
Figure 3B:
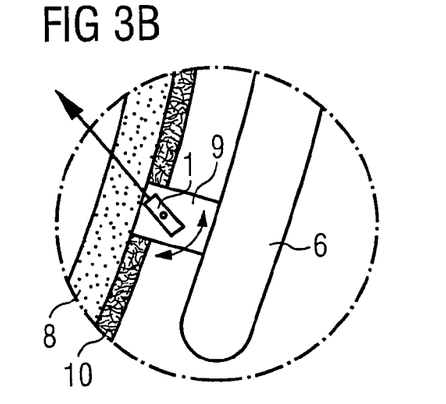

FIG. 3A shows a third embodiment of a brain stimulation system, again with the signal emitters 1 mounted on a common support structure 6. However, in this embodiment the common support structure 6 urges the signal emitters 1 against the patient's cranium 8, just as it urged the paddings 7 against the patient's skin in the embodiment of FIG. 2. FIG. 3B shows the signal emitter 1 in more detail. Accordingly, the signal emitter 1 is movably mounted in a mounting tube 9, the mounting tube 9 being tightly held against the patient's cranium 8 by means of the flexible, but stiff support structure 6. The mounting tube 9, as shown here, penetrates the patient's skin 10 and lies against the cranial bone, so as to prevent any unintentional displacement. Mounting the mounting tube 9 on the patient's skin would cause the signal emitter 1 to be displaced whenever the patient's skin moves on the cranial bone.

The signal emitter 1, as shown in this embodiment, is pivotable about two pivoting axes which are perpendicular to each other, only one of said pivoting axes being schematically indicated by an arrow.

Figure 4A:
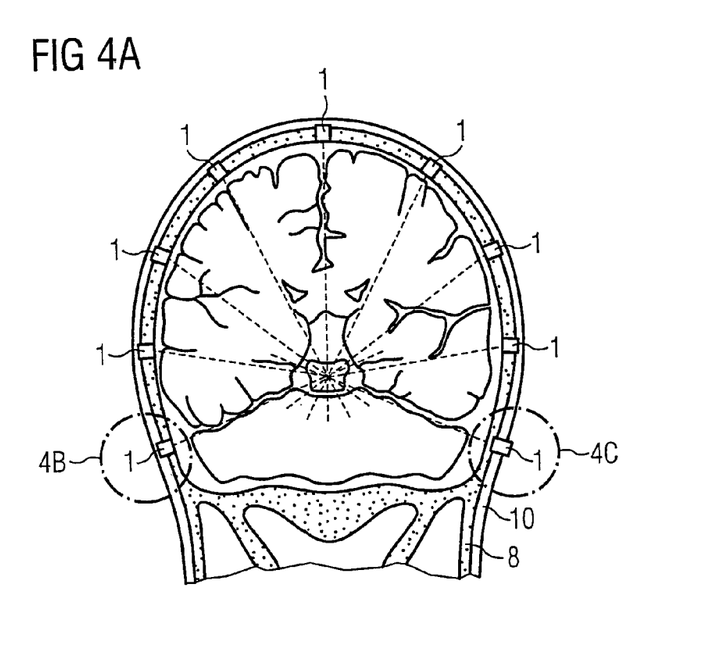
FIGS. 4A to 4C show fourth and fifth embodiments ? (siehe unten) of a brain stimulation system.

FIG. 4A shows (in a single drawing) a fourth and a fifth embodiment of a brain stimulation system. In these embodiments, the signal emitters 1 are permanently fixed in the patient's cranium. A common support structure for the signal emitters 1 is therefore not needed. Shown in these embodiments is also the patient's skin 10 covering the cranium 8. Although not shown in the other embodiments described above, the skin 10 is of course also present there.

Figure 4B:
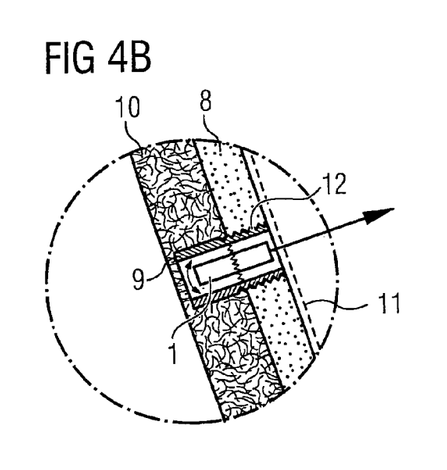

The fourth embodiment shown in FIG. 4A is shown in further detail in FIG. 4B. Accordingly, the signal emitter 1 is again adjustably contained in a mounting tube 9. The mounting tube has a threading 12 on its outside by which it is threaded into and through the cranial bone structure 8 so as to completely penetrate the cranial bone up to the dura mater 11 of the brain, without damaging the dura mater 11. The mounting tube 9 is relatively short and the remainder thereof not penetrating the patient's cranium 8 is covered by the patient's skin 10. Where wireless remote control and/or energy transfer is not possible, galvanic wiring may be provided. Such wiring may also be arranged subcutaneously and, possibly, lead to a control unit in the patient's neck area.

Figure 4C:
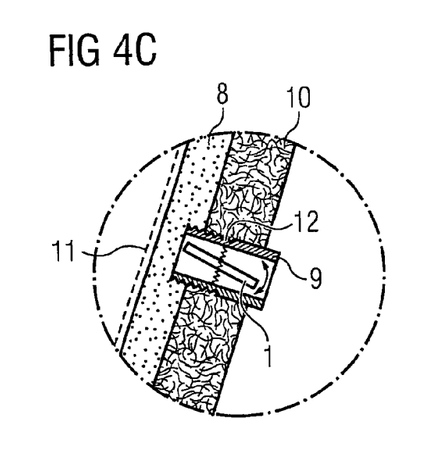

The fifth embodiment of the brain stimulation system shown in FIG. 4A is shown in further detail in FIG. 4C. Again, the signal emitter 1 is pivotably mounted in a mounting tube 9. In this embodiment, however, the mounting tube 9 only reaches into the outer hard layer of the cranial bone without penetrating it completely, and the mounting tube projects through the patient's skin 10 so that it is more easily accessible for conductively providing energy and/or control data.

Figure 5:
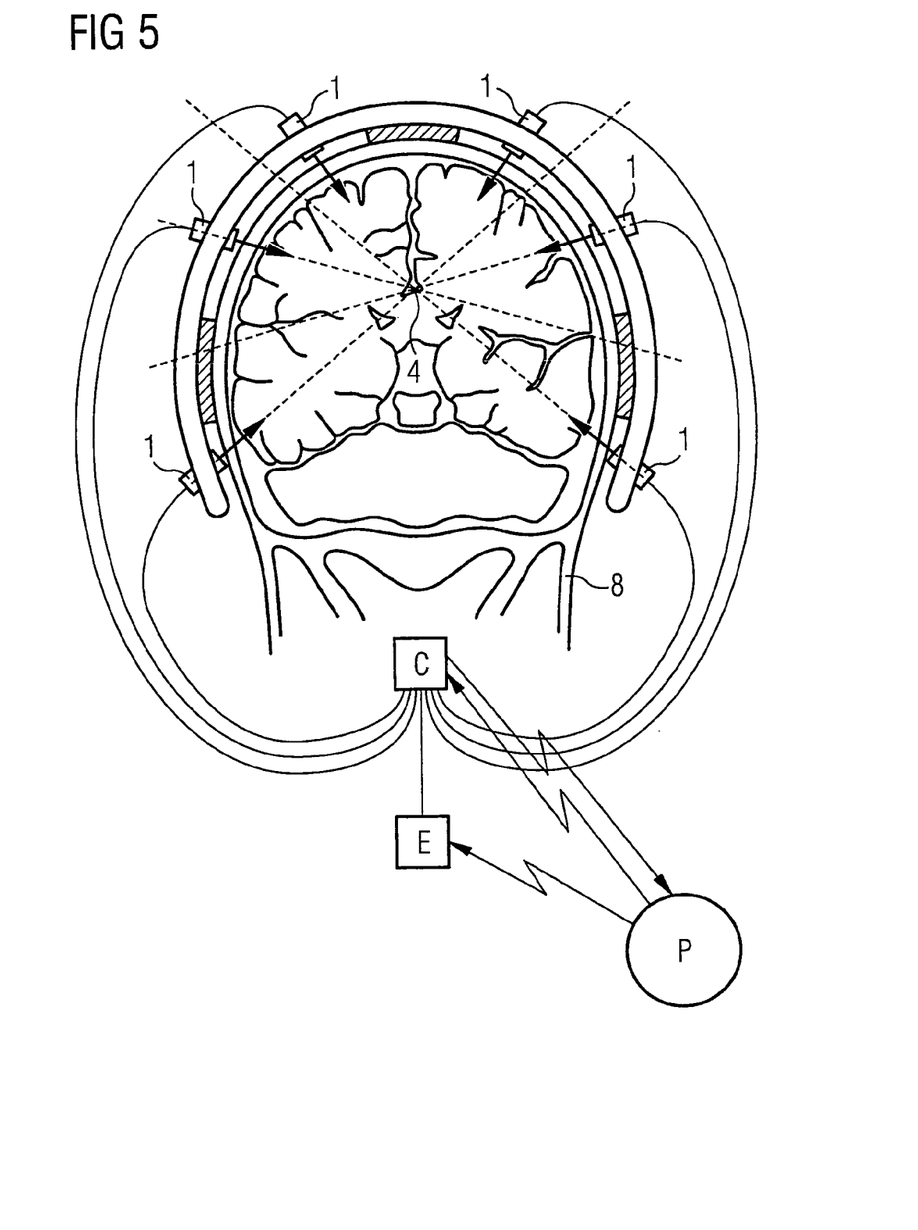
FIG. 5 shows the brain stimulation system of FIG. 2 with control unit, energy supply and programming unit.

FIG. 5 shows an example of a wiring for providing energy and data to the individual signal emitters 1, shown here in context with the second embodiment described above in relation to FIG. 2. Accordingly, each of the signal emitters 1 is connected to a control unit C which is conveniently arranged in the patient's neck area. An energy source E is also connected to the control unit C to provide the control unit C and the signal emitters 1 with energy. A processing unit P remote from the control unit C and energy source E is used to wirelessly provide control data to the control unit C and energy to the energy source E. The control unit C may send feedback data to the processing unit P, the feedback data relating to functional parameters of the system, such as position data of the individual signal emitters 1. In this context, the system further comprises position sensors (not shown) to sense the positions of the individual signal emitters 1.

Where a physical parameter sensor for sensing a physical parameter of the patient is connected to the control unit, the feedback data sent to the processing unit P may further comprise such physical data of the patient.

Figure 6:
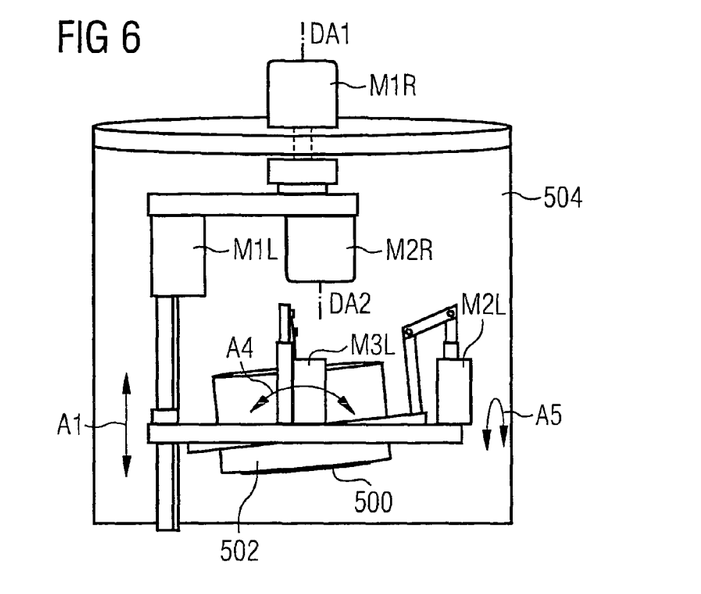
FIGS. 6 to 8 show different views of a signal emitter arrangement.
Figure 7:
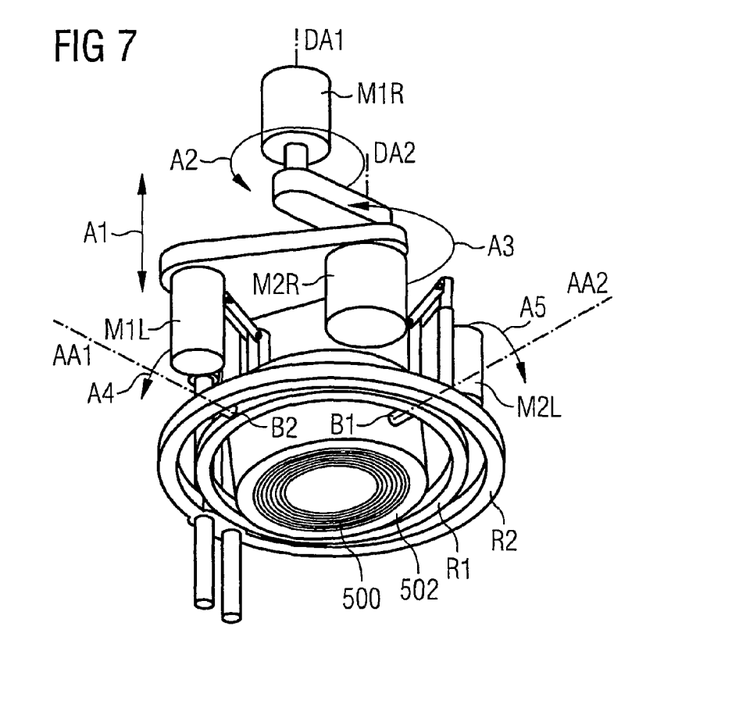
Figure 8:
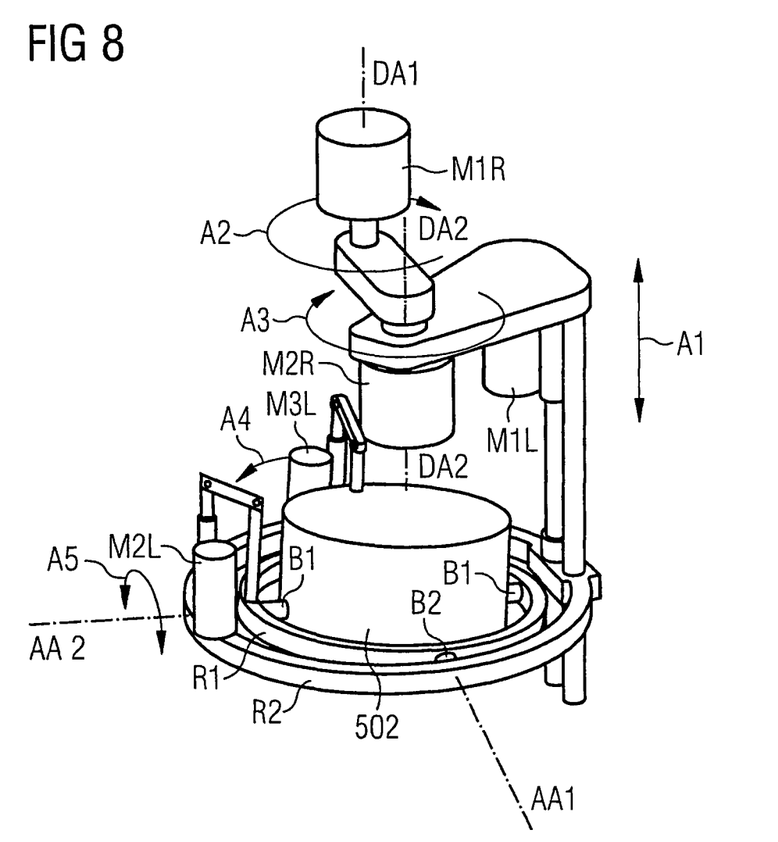

FIGS. 6 to 8 illustrate an embodiment of a signal emitter arrangement. In this case the emitter is a coil displacement unit configured to displace a primary coil 500 in a plurality of different directions. However, the signal emitter can be any kind of emitter. The coil 500 is mounted in a support cylinder 502 which is suspended in a movable manner, as will be described below.

The coil displacement unit comprises plural position adjusting motors mechanically connected to the support cylinder 502 and thereby also to the primary coil 500. Each position adjusting motor further includes some type of position sensor, not shown in FIGS. 6 to 8, adapted to provide position information to a processor, likewise not shown, which corresponds to the external control unit C of FIG. 5. The processor is adapted to control the movement of the primary coil 500, based on a received control signal and on position information from the position sensors.

The coil displacement unit further comprises a housing 504, not shown in FIGS. 7 and 8, supporting and enclosing the position adjusting motors and the primary coil, to allow free movement of the primary coil.

The coil displacement unit further comprises a distance adjusting linear motor M1L for displacing the primary coil in a first direction substantially perpendicular to the patient's cranium, as indicated by arrow A1.

The coil displacement unit further comprises a first distance adjusting rotation motor M1R adapted to displace the primary coil in a second direction substantially parallel to the cranium of said patient by turning the primary coil around a first distance adjustment axis DA1, as indicated by arrow A2.

The coil displacement unit further comprises a second distance adjusting rotation motor M2R adapted to displace the primary coil in the second direction, by turning the primary coil around a second distance adjustment axis DA2 which is substantially parallel to but separate from the first distance adjustment axis DA1, as indicated by arrow A3.

The coil displacement unit further comprises a first angle adjusting linear motor M2L adapted to turn the primary coil around a first angle adjustment axis AA1, as indicated by arrow A4. The first angle adjustment axis is substantially parallel to the patient's cranium, and the motor M2L is adapted to turn the primary coil in a first plane substantially perpendicular to the patient's cranium.

The coil displacement unit further comprises a second angle adjusting linear motor M3L adapted to turn the primary coil around a second angle adjustment axis AA2 perpendicular to the first angle adjustment axis AA3. The second angle adjustment axis AA2 is substantially parallel to the patient's cranium, and the motor M3L is adapted to turn the primary coil in a second plane substantially perpendicular to the patient's cranium and substantially perpendicular to the first plane.

The coil displacement unit further comprises a first ring member R1 inside which the primary coil is mounted by means of opposite first rotation bearings B1 coaxial with the second angle adjustment axis AA2, and a second ring member R2 inside which the first ring member R1 is mounted by means of opposite second rotation bearings 82 coaxial with the first angle adjustment axis AA1, such that the primary coil 500 can be tilted in any direction as a gyro.

The invention claimed is:

1. A therapeutic brain stimulation system, comprising at least two and preferably three or more stimulation signal emitters adapted to generate stimulating signals which in combination allow for wireless stimulation of neuronal cells in a patient's brain, wherein said signal emitters are arranged or adapted to be arranged such that their individual stimulating signals can be emitted from different positions towards a common target region in a patient's brain so as to provide an accumulated stimulating effect on said target region, and wherein the signal emitters are adjustable such that the stimulation signals accumulating in the target region do not negatively affect the anatomic structure of neuronal brain cells in said target region, wherein the signal emitters are adapted to be fixed in cranial bone structure, so as to penetrate only the hard outer layer thereof or so as to completely penetrate the cranial bone structure, wherein each of the signal emitters is contained in a mounting tube with one or more screw threads provided on an outer surface of the mounting tube for fixation in cranial bone structure.

2. The system of claim 1, wherein the signal emitters are adapted to emit the individual stimulation signals in the form of electromagnetic radiation comprising one or more of the following: light waves with a wavelength in the range between infrared and ultraviolet, waves with a wavelength longer than infrared light, and microwaves.

3. The system of claim 1, wherein the individual stimulation signals emitted by the signal emitters are emitted in the form of beams, said beams being directed or directable to cross each other in the target region.

4. The system of claim 3, further comprising focusing devices for focusing the beams onto the target region.

5. The system of claim 1, wherein the signal emitters are adapted to emit the individual stimulation signals in the form of sound waves.

6. The system of claim 1, wherein the signal emitters are adapted to emit the individual stimulation signals in the form of electromagnetic fields.

7. The system of claim 1, wherein the signal emitter comprises a helical winding around a symmetry axis adapted to be directed through said target region.

8. The system of claim 1, wherein the orientation of the signal emitter inside the mounting tube is adjustable.

9. The system of claim 1, comprising at least one position adjusting motor for each of the signal emitters for individually adjusting the signal emitters relative to a target to be stimulated.

10. The system of claim 9, wherein each of said at least one position adjusting motor includes a position sensor adapted to provide position information to a control unit.

11. The system of claim 1, wherein the control unit includes a position controller adapted to control the adjustment of the positions of the signal emitters relative to a target region to be stimulated.

12. The system of claim 1 further comprising a control unit, and wherein the control unit includes a signal emission controller for controlling the generation of stimulating signals emitted by the signal emitters, and wherein the signal emission controller is adapted to control one or more of the following parameters of the emitted stimulating signals: timing, sequence, intensity, frequency, duration.

13. The system of claim 12 further comprising a physical parameter sensor for sensing a physical parameter of the patient, wherein said signal emission controller is adapted to control the adjustment of the stimulating signal in response to a sensor signal of the physical parameter sensor.

14. The system of claim 12 further comprising a functional parameter sensor for sensing a functional parameter of the system, wherein said signal emission controller is adapted to control the adjustment of the stimulating signal in response to a sensor signal of the functional parameter sensor.

15. The system of claim 12, wherein the signal emission controller comprises a manually operable switch for turning on and off the system, said switch being adapted for subcutaneous implantation so as to be manually operable from outside the patient's body.

16. The system of claim 12, wherein the signal emission controller is adapted to control sequential stimulation of different target region areas, or wherein the signal emission controller is adapted to shift over time the stimulation from one of the target region areas to another one of the target region areas.

17. The system of claim 16, wherein the signal emission controller is adapted to control emission of the stimulation signals in the form of pulse trains such that at least a first area and a second area of the target region areas are repeatedly stimulated with a first pulse train and a second pulse train, respectively, with said first and second pulse trains being shifted over time relative to each other.

18. The system of claim 12, wherein the signal emission controller is adapted to control emission of the stimulating signals in the form of pulse trains so as to vary one or more of the following: the amplitudes of the pulses of the pulse trains, the off time periods between the pulses of the pulse trains, the frequency of said pulse trains, the frequency of the pulses within the pulse trains, the width of the pulses of the pulse trains, the off time periods between the pulse trains, the length of each pulse train, and the number of pulses of the pulse trains.

19. The system of claim 1 further comprising a control unit, and wherein the control unit comprises a first part adapted to be mounted to the patient's cranium along with the signal emitters and a second part for remote communication with the first part, and wherein the second part of the control unit is adapted to wirelessly transmit control signals to the first part of the control unit.

20. The system of claim 1 further comprising at least one energy transformer connected to the signal emitters for transforming wireless energy into electric energy and for supplying the electric energy directly or indirectly to the signal emitters, and an energy transmitter for wirelessly transmitting energy to the at least one energy transformer.

21. The system of claim 1 further comprising a catalyst for implantation inside the patient's brain, wherein the catalyst comprises a piece of metal.

22. The system of claim 1, wherein the signal emitters (1) are arranged or arrangeable at an equal distance from the target region.

23. The system of claim 1, wherein the signal emitters (1) are arranged or arrangeable at a phase-correct distance relative to the target region.

24. The system of claim 5, wherein the signal emitters (1) are adjusted or adjustable so that their respective electromagnetic fields overlap each other with collinear induced current directions in the target region (4).

25. The system of claim 1, wherein the signal emitters are adapted to emit the individual stimulation signals in the form of electromagnetic radiation.

26. The system of claim 1, wherein the signal emitters are adapted to emit the individual stimulation signals in the form of electromagnetic radiation comprising a wavelength longer than infrared light.

27. The system of claim 1, wherein the signal emitters are adapted to be implanted so as not to penetrate the skin after implantation.

28. The system of claim 1, wherein the orientation of the signal emitter inside the mounting tube is adjustable and wherein the signal emitters are adapted to be implanted so as not to penetrate the skin after implantation.

29. A method of mounting a therapeutic brain stimulation system, onto a patient's head, the method comprising the steps of:
cutting the patient's skin at two or more different positions above the patient's cranial bone structure adjacent the patient's brain,
attaching a signal emitter to the patient's cranium, directly or indirectly, at each of the different positions, said signal emitters being adapted to generate stimulating signals which in combination allow for wireless stimulation of neuronal cells in the patient's brain, and
adjusting said signal emitters such that their individual stimulating signals are emitted from said different positions towards a common target region in the patient's brain so as to provide an accumulated stimulating effect on that target region, said accumulated stimulating effect on the target region being adjusted so as not to negatively affect the anatomic structure of neuronal brain cells
wherein the step of attaching the signal emitters to the patient's cranium includes fixing the signal emitters in the cranial bone structure so as to penetrate only the hard outer layer thereof, or fixing the signal emitters in cranial bone structure so as to completely penetrate the cranial bone structure without penetrating into the dura mater of the brain
wherein the signal emitters comprise one or more screw threads and the step of permanently mounting the signal emitters to the patient's cranium includes screwing the signal emitters in the cranial bone structure, and wherein each of the signal emitters is contained in a mounting tube with the screw threads provided on an outer surface of the mounting tube.

30. The method of claim 29 further comprising the step of placing in the target region a piece of material as a catalyst which causes an increased accumulated stimulation in the target region.

31. The method of claim 29, comprising the steps of; implanting the signal emitters not penetrating the skin (1) after implantation.

\* \* \* \* \*